(12) United States Patent
Kolczewski et al.

(10) Patent No.: US 8,044,047 B2
(45) Date of Patent: Oct. 25, 2011

(54) 5-SUBSTITUTED BENZOXAZINES

(75) Inventors: Sabine Kolczewski, Loerrach (DE); Olivier Roche, Folgensbourg (FR); Lucinda Steward, Basel (CH); Juergen Wichmann, Steinen (DE); Thomas Woltering, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 238 days.

(21) Appl. No.: 12/549,687

(22) Filed: Aug. 28, 2009

(65) Prior Publication Data
US 2010/0063042 A1 Mar. 11, 2010

(30) Foreign Application Priority Data
Sep. 8, 2008 (EP) .................................... 08163832

(51) Int. Cl.
C07D 265/02 (2006.01)
C07D 413/04 (2006.01)
A61K 31/536 (2006.01)

(52) U.S. Cl. ...................... 514/230.5; 544/90
(58) Field of Classification Search .................. 544/90; 514/230.5
See application file for complete search history.

(56) References Cited

FOREIGN PATENT DOCUMENTS
JP 09255665 A * 9/1997
WO WO 2004/096771 11/2004
WO WO 2005/067933 7/2005
WO WO 2008/068157 6/2008

OTHER PUBLICATIONS

Hoyer et al., Pharmacol. Rev. vol. 46 pp. 157-204 (1994).
Rees et al., FEBS Letters vol. 355, pp. 242-246 (1994).
Francken et al., Eur. J. Pharmacol. vol. 261, pp. 299-309 (1998).
Noda et al., J. Neurochem. vol. 84, pp. 222-232 (2003).
Thomas, D., Pharmacology & Therapeutics vol. 111, pp. 707-714 (2006).
Doly et al., Journal of Comparative Neurology vol. 476, pp. 316-329 (2004).
Dubertret et al., Journal of Psychiatric Research vol. 38, pp. 371-376 (2004).
Nair et a., Tetrahedron Letters vol. 47, pp. 3953-3955 (2006).
You et al., Bulletin of the Korean Chem. Society vol. 22(11) pp. 1270-1272 (2001).
Gauss, W. K., *Synthesis*, (1978 DE) 5: 377-379 XP002553473.

* cited by examiner

*Primary Examiner* — Kahsay T Habte
(74) *Attorney, Agent, or Firm* — George W. Johnston; Patricia S. Rocha-Tramaloni; Kimberly J. Prior

(57) ABSTRACT

The present invention is concerned with 5-substituted benzoxazine derivatives of formula (I)

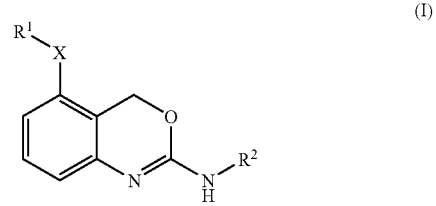

wherein X, $R^1$ and $R^2$ are as described herein, as well as their manufacture, pharmaceutical compositions containing them. Compounds of the present invention are $5\text{-}HT_{5A}$ receptor antagonists, and are useful in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

15 Claims, No Drawings

US 8,044,047 B2

5-SUBSTITUTED BENZOXAZINES

PRIORITY TO RELATED APPLICATION(S)

This application claims the benefit of European Patent Application No. 08163832.2, filed Sep. 8, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-HT$_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the 5-HT$_{5A}$ receptor in the rat spinal cord that 5-HT$_{5A}$ receptors may play a role in central motor control, nociception and autonomic function such as stress induced urinary incontinence and overactive bladder. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides 5-substituted benzoxazine derivatives as 5-HT$_{5A}$ receptor antagonists, their manufacture, pharmaceutical compositions containing them and their use in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

In particular, the present invention is concerned with compounds of the general formula (I)

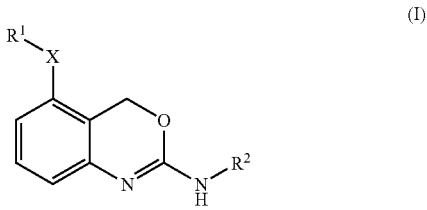

wherein
X is a bond, —NH—, —NH—S(O)$_2$—, or —NH—C(O)—CH$_2$—;
R$^1$ is halo, C$_{1-7}$-alkyl, —NR$^a$R$^b$, cyano, nitro, or is phenyl or 3- to 8-membered cycloalkyl, each of which is optionally substituted by one or more halo;
R$^2$ is C$_{3-8}$-cycloalkyl or a 5- or 6-membered heterocycloalkyl, each optionally anellated with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;
R$^a$ and R$^b$ is each independently hydrogen or C$_{1-7}$-alkyl;

The compounds of formula (I) can contain asymmetric carbon atoms. Accordingly, the present invention includes all stereoisomeric forms of the compounds of formula (I), including each of the individual enantiomers and mixtures thereof, i.e. their individual optical isomers and mixtures thereof.

The invention also provides pharmaceutical compositions containing compounds of the invention and a pharmaceutically acceptable carrier. The invention further provides methods for the manufacture of the compounds and compositions of the invention.

Compounds of formula (I) have good activity on the 5-HT$_{5A}$ receptor. Therefore, the invention provides methods for the treatment of depression (which term includes bipolar depression, unipolar depression, single or recurrent major depressive episodes with or without psychotic features, catatonic features, melancholic features, atypical features or post-partum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

Unless otherwise indicated, the following definitions are set forth to illustrate and define the meaning and scope of the various terms used to describe the invention herein.

The following definitions of the general terms apply irrespective of whether the terms in question appear alone or in combination. It must be noted that, as used in the specification and the appended claims, the singular forms "a", "an," and "the" include plural forms unless the context clearly dictates otherwise.

As used herein, the term "$C_{1-7}$-alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred $C_{1-7}$ alkyl groups are groups with 1, 2, 3 or 4 carbon atoms. Particularly preferred is methyl.

The term "$C_{1-7}$-alkoxy" denotes a group —O—R' wherein R' is $C_{1-7}$-alkyl as defined above, preferably methoxy.

The term "halo" denotes chloro, iodo, fluoro and bromo. Preferred halo are fluoro, chloro and bromo, more preferred are fluoro and chloro.

The term "cycloalkyl" refers to a monovalent saturated monocyclic or bicyclic hydrocarbon radical of 3 to 8 ring carbon atoms. Bicyclic means consisting of two saturated carbocycles having two carbon atoms in common, i.e. the bridge separating the two rings is either a single bond or a chain of preferably one or two carbon atoms. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, and bicyclo[2.2.2]octanyl. Preferred cycloalkyl is a monocyclic hydrocarbon radical of 3 to 6 ring carbon atoms, and preferred examples are cyclopropyl, cyclopentyl and cyclohexyl. Particularly preferred are cyclopropyl and cyclopentyl.

The term "5- or 6-membered heterocycloalkyl" refers to a monovalent saturated monocyclic ring system. Preferably, 5- or 6-membered heterocycloalkyl is a monovalent saturated monocyclic ring containing one or two ring heteroatoms selected from N, O, and S. Examples for 5- or 6-membered heterocycloalkyl moieties are tetrahydropyranyl, tetrahydrothiopyranyl, tetrahydrofuranyl, tetrahydrothiophenyl, pyrrolidinyl, imidazolidinyl, morpholinyl, thiomorpholinyl, piperidinyl, and piperazinyl. Preferred examples are morpholinyl, piperidinyl or piperazinyl. The 5- or 6-membered heterocycloalkyl moiety is optionally substituted as described herein. Among the preferred heterocycloalkyls is tetrahydrofuranyl.

The term "5- or 6-membered heteroaryl" as defined herein denotes a monovalent monocyclic or bicyclic, preferably monocyclic, aromatic ring system of 5 or 6 ring atoms containing one, two, or three ring heteroatoms selected from N, O, and S, the remaining ring atoms being C. Examples of heteroaryl moieties include, but are not limited to thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl or pyridazinyl. A preferred example for heteroaryl is furanyl. The heteroaryl may be optionally substituted as defined herein and are in principle the same as those for phenyl. Examples for substituents on heteroaryl include, but are not limited to $C_{1-7}$-alkyl, cycloalkyl, $C_{1-7}$-alkoxy, haloalkoxy, haloalkyl, halo, OH, CN, or an anellated bridge being selected from —O—CH$_2$CH$_2$O—, —O—CHCH$_3$CH$_2$—, and —O—C(CH$_3$)$_2$CH$_2$—. Preferred substituents on heteroaryl are $C_{1-7}$-alkyl or $C_{1-7}$-alkoxy.

Analogously to the heteroaryl system, Phenyl can be unsubstituted or substituted with one or more substituents selected from $C_{1-7}$-alkyl, cycloalkyl, $C_{1-7}$-alkoxy, haloalkoxy, haloalkyl, halo, OH, CN, or an anellated bridge being selected from —O—CH$_2$CH$_2$O—, —O—CHCH$_3$CH$_2$—, and —O—C(CH$_3$)$_2$CH$_2$—. Preferred substituents on phenyl are halo or $C_{1-7}$-alkoxy. Particularly preferred substituents on phenyl are fluoro, chloro or methoxy.

The term "substituted", unless specifically defined otherwise, means that the specified group or moiety can bear 1, 2, 3, 4, 5 or 6 substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. One or two substituents are preferred, unless specifically defined otherwise.

The term "haloalkyl" means a lower alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred haloalkyl groups are difluoro- or trifluoro-methyl or -ethyl.

The term "haloalkoxy" means a lower alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

As used herein, the term "thiophenyl" is synonymous with "thienyl" and each represents a thiophene substituent, i.e., $C_4H_4S$.

"Pharmaceutically acceptable," such as pharmaceutically acceptable carrier, excipient, etc., means pharmacologically acceptable and substantially non-toxic to the subject to which the particular compound is administered.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

"Therapeutically effective amount" means an amount that is effective to prevent, alleviate or ameliorate symptoms of disease or prolong the survival of the subject being treated.

In detail, the present invention provides compounds of formula (I)

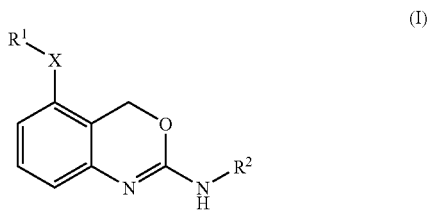

wherein:
X is a bond, —NH—, —NH—S(O)$_2$—, or —NH—C(O)—CH$_2$—;
R$^1$ is halo, C$_{1-7}$-alkyl, —NR$^a$R$^b$, cyano, nitro, or is phenyl or 3- to 8-membered cycloalkyl, each of which is optionally substituted by one or more halo;
R$^2$ is cycloalkyl or 5- or 6-membered heterocycloalkyl, each optionally anellated with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;
R$^a$ and R$^b$ is each independently hydrogen or C$_{1-7}$-alkyl;
or a pharmaceutically acceptable salt thereof.

In certain embodiments of the compound of formula (I), X is a bond, —NH—, —NH—S(O)$_2$—, or —NH—C(O)—CH$_2$—;
R$^1$ is halo, C$_{1-7}$-alkyl, —NH$_2$, cyano, nitro, cyclopropyl or phenyl optionally substituted by one or more halo;
R$^2$ is cyclopentyl or 5- or 6-membered heterocycloalkyl, each optionally anellated with phenyl;
which is optionally substituted with one or more C$_{1-7}$-alkoxy.

In certain embodiments of the compound of formula (I), X is a bond, —NH—, or —NH—S(O)$_2$—;
R$^1$ is C$_{1-3}$-alkyl, —NH$_2$, cyclopropyl or phenyl optionally substituted by one or more halo;
R$^2$ is

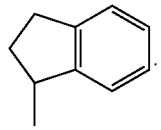

In certain embodiments of the compound of formula (I), X is a bond, —NH—, —NH—C(O)—CH$_2$— or —NH—S(O$_2$)—. Even more preferred compounds of the present invention are those, wherein X is —NH— or —NH—C(O)—CH$_2$—.

In certain embodiments of the compound of formula (I), R$^1$ is halo, C$_{1-7}$-alkyl, —NH$_2$, cyano, nitro, 3- to 8-membered cycloalkyl, or phenyl substituted by one or more halo. Even more preferred compounds of the present invention are those, wherein R$^1$ is C$_{1-7}$-alkyl, —NH$_2$, 3- to 8-membered cycloalkyl, or phenyl substituted by one or two halo. Most preferred are compounds wherein R$^1$ is methyl, NH$_2$, 4-fluoro-phenyl, 4-chloro-phenyl, 3,5-difluoro-phenyl or cyclopropyl.

In certain embodiments of the compound of formula (I), R$^2$ is 3-8 membered cycloalkyl or 5- or 6-membered heterocycloalkyl anellated with phenyl, which is optionally substituted with one or more C$_{1-7}$-alkoxy. Even more preferred compounds of the present invention are those, wherein R$^2$ is 3-8 membered cycloalkyl anellated with phenyl. Most preferred are compounds wherein R$^2$ is indan-1-yl.

Preferred compounds of present invention are those wherein R$^2$ is

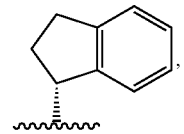

and wherein R$^2$ is present as (R)-stereoisomer.

In certain embodiments of the compound of formula (I) X is a bond, —NH—, —NH—S(O)$_2$—, or —NH—C(O)—CH$_2$—;
R$^1$ is halo, C$_{1-7}$-alkyl, —NR$^a$R$^b$, cyano, nitro, or is phenyl or 3- to 8-membered cycloalkyl, each of which is optionally substituted by one or more halo;
R$^2$ is cyclopentyl or a 5-or 6-membered heterocycloalkyl, each optionally anellated with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;
R$^a$ and R$^b$ is each independently hydrogen or C$_{1-7}$-alkyl;
or a pharmaceutically acceptable salt thereof.

In certain embodiments of the compound of formula (I) X is a bond, —NH—, —NH—S(O)$_2$—, or —NH—C(O)—CH$_2$—;
R$^1$ is halo, C$_{1-7}$-alkyl, —NH$_2$, cyano, nitro, cyclopropyl or phenyl optionally substituted by one or more halo;
R$^2$ is cyclopentyl or a 5- or 6-membered heterocycloalkyl, each optionally anellated with phenyl, which is optionally substituted with one or more C$_{1-7}$-alkoxy.

In particular, preferred compounds are the compounds of formula (I) described in the examples as individual compounds as well as pharmaceutically acceptable salts thereof. Furthermore, the substituents as found in the specific examples described below, individually constitute separate preferred embodiments of the present invention.

Preferred compounds of formula (I) are:
(5-Chloro-4H-benzo[d][1,3]oxazin-2-yl)-(R)-indan-1-yl-amine;
(R)-Indan-1-yl-(5-nitro-4H-benzo[d][1,3]oxazin-2-yl)-amine;
(R)—N$^2$-Indan-1-yl-4H-benzo[d][1,3]oxazine-2,5-diamine;
N$^2$-(4-Methoxy-2,3-dihydro-benzofuran-3-yl)-4H-benzo[d][1,3]oxazine-2,5-diamine;
2-(4-Chloro-phenyl)-N-[2-((R)-indan-1-ylamino)-4H-benzo[d][1,3]oxazin-5-yl]-acetamide;
3,5-Difluoro-N-[2-((R)-indan-1-ylamino)-4H-benzo[d][1,3]oxazin-5-yl]-benzenesulfonamide;

3,5-Difluoro-N-[2-(4-methoxy-2,3-dihydro-benzofuran-3-ylamino)-4H-benzo[d][1,3]oxazin-5-yl]-benzenesulfonamide;
Cyclopropanesulfonic acid [2-((R)-indan-1-ylamino)-4H-benzo[d][1,3]oxazin-5-yl]-amide;
(5-Bromo-4H-benzo[d][1,3]oxazin-2-yl)-(R)-indan-1-yl-amine;
N-[2-((R)-Indan-1-ylamino)-4H-benzo[d][1,3]oxazin-5-yl]-methanesulfonamide;
2-((R)-Indan-1-ylamino)-4H-benzo[d][1,3]oxazine-5-carbonitrile;
(5-Cyclopropyl-4H-benzo[d][1,3]oxazin-2-yl)-(R)-indan-1-yl-amine;
[5-(4-Fluoro-phenyl)-4H-benzo[d][1,3]oxazin-2-yl]-(R)-indan-1-yl-amine;
$N^5$-(4-Fluoro-phenyl)-$N^2$—(R)-indan-1-yl-4H-benzo[d][1,3]oxazine-2,5-diamine; and
$N^5$-(4-Chloro-phenyl)-$N^2$—(R)-indan-1-yl-4H-benzo[d][1,3]oxazine-2,5-diamine,
and pharmaceutically acceptable salts thereof.

Even more preferred compounds of formula (I) of present invention are those selected from the group consisting of:
(R)—$N^2$-Indan-1-yl-4H-benzo[d][1,3]oxazine-2,5-diamine;
3,5-Difluoro-N-[2-((R)-indan-1-ylamino)-4H-benzo[d][1,3]oxazin-5-yl]-benzenesulfonamide;
Cyclopropanesulfonic acid [2-((R)-indan-1-ylamino)-4H-benzo[d][1,3]oxazin-5-yl]-amide;
N-[2-((R)-Indan-1-ylamino)-4H-benzo[d][1,3]oxazin-5-yl]-methanesulfonamide;
$N^5$-(4-Fluoro-phenyl)-$N^2$—(R)-indan-1-yl-4H-benzo[d][1,3]oxazine-2,5-diamine; and
$N^5$-(4-Chloro-phenyl)-$N^2$—(R)-indan-1-yl-4H-benzo[d][1,3]oxazine-2,5-diamine,
and pharmaceutically acceptable salts thereof.

The present compounds of formula (I), their starting materials, their pharmaceutically acceptable salts, and their optical isomers can be prepared by methods known in the art. For example, a process to synthesize representative compounds of formula (1) wherein $R^1$, $R^2$ and X have meanings as given above, may comprise one of the following steps:

a) protecting the alcohol function of compound (1),

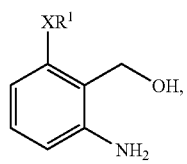
(1)

wherein $R^1$ and X are as defined above, preferably by reacting compound (1) with a silyl group containing compound, more preferably tert-butyldimethylsilyl or tert-butyldiphenylsilyl, to yield compound (2)

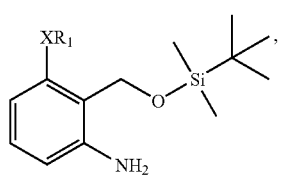
(2)

wherein the alcohol function is protected with a silyl protecting group;

b) transforming the amino group of compound (2) wherein $R^1$ and X are as defined above, into an isothiocyanate, preferably by reacting compound (2) with thiophosgene in the presence of sodium hydrogen carbonate in a chlorinated solvent, more preferably dichloromethane or chloroform, to yield compound (3)

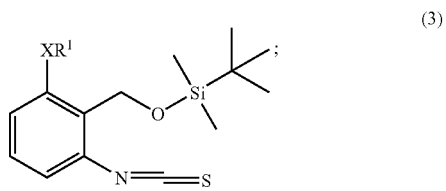
(3)

c) reacting compound (3), wherein $R^1$ and X are as defined above, with an amine $H_2N$—$R^2$, wherein $R^2$ is as defined above, to yield compound (4)

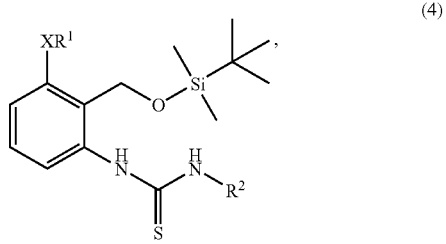
(4)

wherein the reaction between the isothiocyanate function of compound (3) and the amino function of $H_2N$—$R^2$ forms a thiourea function in compound (4);

d) removing the alcohol function protecting group of compound (4), wherein $R^1$, $R^2$ and X are as defined above, preferably by reacting compound (4) with a fluoride compound, more preferably tetrabutylammonium fluoride to yield the (2-hydroxymethyl-phenyl)-thiourea of general formula (5)

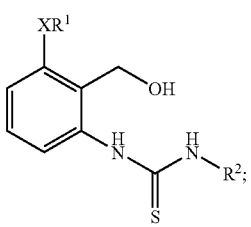
(5)

e) and reacting the (2-hydroxymethyl-phenyl)-thiourea of general formula (5), wherein $R^1$, $R^2$ and X are as defined above, with a carbodiimide reagent, preferably 1-(3-dimethylaminopropyl)-3-ethylcarbodiimide hydrochloride, dicyclohexylcarbodiimide or diisopropylcarbodiimide to yield the 4H-benzo[d][1,3]oxazin-2yl-amine of general formula (I).

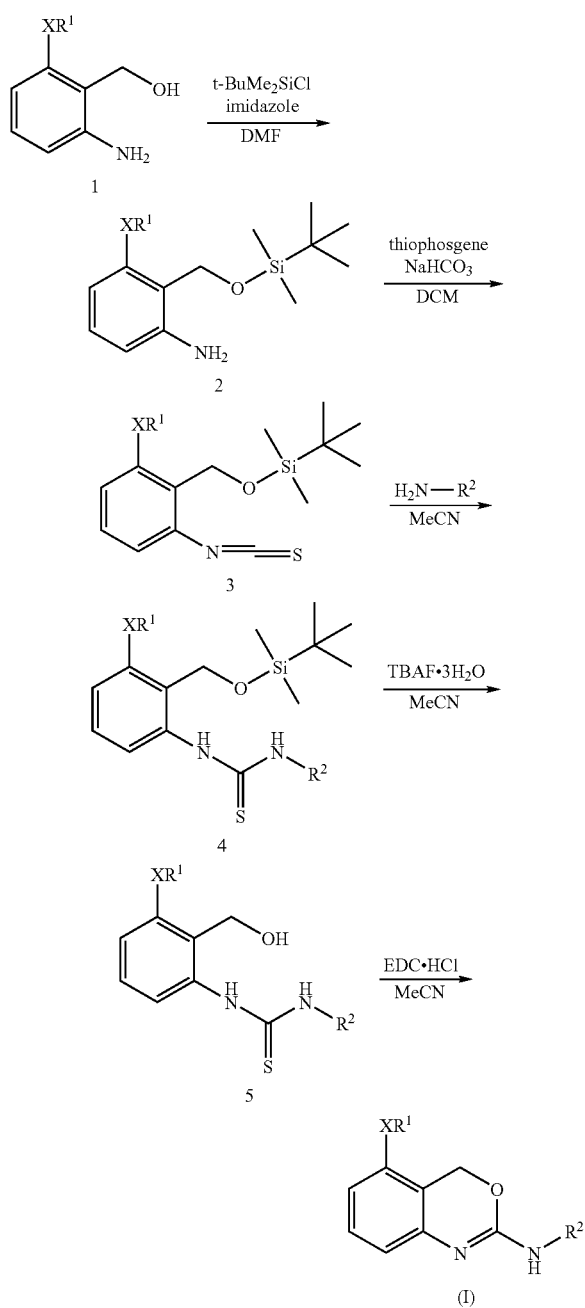

Scheme 1

In accordance with scheme 1, compounds of formula (I) can be prepared as shown in the following description of the general synthesis of 4H-benzo[d][1,3]oxazin-2yl-amines:

The alcohol function of a 2-aminobenzyl alcohol with the general formula (1) substituted in 6-position with X—$R^1$, and wherein X and $R^1$ are defined as described above, is protected with a silyl protecting group, like e.g. tert-butyldimethylsilyl or tert-butyldiphenylsilyl, by reaction with the corresponding chlorosilane, like e.g. tert-butyldimethyl(chloro)silane (t-BuMe$_2$SiCl) or tert-butyldiphenyl(chloro)silane, in the presence of a base, like e.g. imidazole or the combination of either triethylamine or diisopropylethylamine with 4-dimethylaminopyridine or imidazole, in an organic solvent, like e.g. dimethylformamide (DMF), dimethylacetamide or N-methylpyrrolidinone, at temperatures between 0 and 40° C. to produce compounds of general formula (2). The amino group of compounds of general formula (2) in which X and $R^1$ are defined as described above is transformed into an isothiocyanate of general formula (3) in which X and $R^1$ are defined as described above by reaction with e.g. thiophosgene in the presence of sodium hydrogen carbonate in a chlorinated solvent, like e.g. dichloromethane (DCM) or chloroform, at temperatures between 0 and 35° C. as e.g. described in *Tetrahedron Letters* 2006, 47, 3953. The isothiocyanate of general formula (3) in which X and $R^1$ are defined as described above is then reacted with an amine of general formula $R^2$—$NH_2$ in which $R^2$ is defined as described above in an organic solvent, like e.g. acetonitrile (MeCN) or tetrahydrofuran, at temperatures between −20 and 50° C. to produce thioureas of general formula (4) in which X, $R^1$ and $R^2$ are as described above. The silyl protecting group in compounds of general formula (4) in which X, $R^1$ and $R^2$ are as described above is then removed by treatment with a fluoride source, like e.g. tetrabutylammonium fluoride (TBAF), in an organic solvent, like e.g. acetonitrile, tetrahydrofuran or dichloromethane, at temperatures between −20 and 35° C. to give compounds of the general formula (5) in which X, $R^1$ and $R^2$ are as described above. These (2-hydroxymethyl-phenyl)-thioureas of general formula (5) in which X, $R^1$ and $R^2$ are as described above are then treated with a carbodiimide reagent, like e.g. 1-(3-dimethylaminopropyl)-3-ethylcarbodiimide hydrochloride (EDC.HCl), dicyclohexylcarbodiimide (DCC) or diisopropylcarbodiimide, in an organic solvent, like e.g. acetonitrile or tetrahydrofuran, at temperatures between 50 and 90° C. to yield the desired 4H-benzo[d][1,3]oxazin-2yl-amines of general formula (1) in which X, $R^1$ and $R^2$ are as described above. A similar procedure for this cyclization can be found in *Bulletin of the Korean Chemical Society* 2001, 22(11), 1270. The steps reacting the isothiocyanate of general formula 3 in which X and $R^1$ are defined as described above with an amine of general formula $R^2$—$NH_2$ in which $R^2$ is defined as described above until the final isolation of the desired 4H-benzo[d][1,3]oxazin-2yl-amines of general formula (1) in which X, $R^1$ and $R^2$ are as described above can be performed in one reaction vessel by successive addition of the reagents as described above. Experimental details can be found in the corresponding examples.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

It will be appreciated that the compounds of general formula (I) in this invention can be derivatized at functional groups to provide derivatives which are capable of conversion back to the parent compound in vivo.

As mentioned earlier, the compounds of formula (I) and their pharmaceutically acceptable addition salts possess valuable pharmaceutical properties. Compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The invention therefore also relates to a pharmaceutical composition comprising at least one compound of formula (I) and a pharmaceutically acceptable excipient, especially for the use in the prevention or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders.

The invention likewise embraces a compound of formula (I) for use as therapeutically active substances, especially as therapeutically active substances for the treatment or prevention of diseases which are related to the 5-HT$_{5A}$ receptor, particularly for the treatment or prevention of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders.

In another preferred embodiment, the invention relates to a method for the treatment or prevention of diseases which are related to the 5-HT$_{5A}$ receptor, particularly for the treatment or prevention of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders, which method comprises administering a compound as defined above to a human being or animal.

The invention also relates to the use of a compound of formula (I) for the manufacture of the pharmaceutical compositions of the invention which are useful for the treatment or prevention of diseases which are related to the 5-HT$_{5A}$ receptor, particularly for the treatment or prevention of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders. Such medicaments comprise a compound as described above.

The treatment or prevention of depression, anxiety, sleep disorders and schizophrenia is preferred.

The compounds were investigated in accordance with the test given hereinafter:

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and K$_i$ values calculated using the Cheng-Prussoff equation.

The activity of the compounds according to the invention is exemplified in table 1 below.

TABLE 1

| Example | Systematic Name | K$_i$/µM |
|---|---|---|
| 1 | (5-Chloro-4H-benzo[d][1,3]oxazin-2-yl)-(R)-indan-1-yl-amine | 0.057 |
| 2 | (R)-Indan-1-yl-(5-nitro-4H-benzo[d][1,3]oxazin-2-yl)-amine | 0.169 |
| 3 | (R)—N$^2$-Indan-1-yl-4H-benzo[d][1,3]oxazine-2,5-diamine | 0.003 |
| 4 | N$^2$-(4-Methoxy-2,3-dihydro-benzofuran-3-yl)-4H-benzo[d][1,3]oxazine-2,5-diamine | 0.027 |
| 5 | 2-(4-Chloro-phenyl)-N-[2-((R)-indan-1-ylamino)-4H-benzo[d][1,3]oxazin-5-yl]-acetamide | 0.131 |
| 6 | 3,5-Difluoro-N-[2-((R)-indan-1-ylamino)-4H-benzo[d][1,3]oxazin-5-yl]-benzenesulfonamide | 0.002 |
| 7 | 3,5-Difluoro-N-[2-(4-methoxy-2,3-dihydro-benzofuran-3-ylamino)-4H-benzo[d][1,3]oxazin-5-yl]-benzenesulfonamide | 0.010 |
| 8 | Cyclopropanesulfonic acid [2-((R)-indan-1-ylamino)-4H-benzo[d][1,3]oxazin-5-yl]-amide | 0.002 |
| 9 | (5-Bromo-4H-benzo[d][1,3]oxazin-2-yl)-(R)-indan-1-yl-amine | 0.106 |
| 10 | N-[2-((R)-Indan-1-ylamino)-4H-benzo[d][1,3]oxazin-5-yl]-methanesulfonamide | 0.005 |
| 11 | 2-((R)-Indan-1-ylamino)-4H-benzo[d][1,3]oxazine-5-carbonitrile | 0.118 |
| 12 | (5-Cyclopropyl-4H-benzo[d][1,3]oxazin-2-yl)-(R)-indan-1-yl-amine | 0.013 |
| 13 | [5-(4-Fluoro-phenyl)-4H-benzo[d][1,3]oxazin-2-yl]-(R)-indan-1-yl-amine | 0.078 |

TABLE 1-continued

| Example | Systematic Name | $K_i/\mu M$ |
|---|---|---|
| 14 | $N^5$-(4-Fluoro-phenyl)-$N^2$-(R)-indan-1-yl-4H-benzo[d][1,3]oxazine-2,5-diamine | 0.003 |
| 15 | $N^5$-(4-Chloro-phenyl)-$N^2$-(R)-indan-1-yl-4H-benzo[d][1,3]oxazine-2,5-diamine | 0.002 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
|---|---|---|---|---|---|
| 1. | Compound of formula (I) | 5 | 25 | 100 | 500 |
| 2. | Anhydrous Lactose | 125 | 105 | 30 | 150 |
| 3. | Corn Starch | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples 1 to 15 are provided for illustration of the invention. They should not be considered as limiting the scope of the invention, but merely as being representative thereof.

INTERMEDIATE 1

2-(tert-Butyl-dimethyl-silanyloxymethyl)-3-nitro-phenylamine

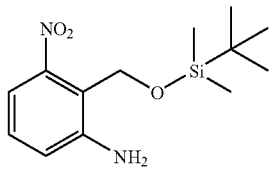

To a mixture of (2-amino-6-nitro-phenyl)-methanol (CAS 98451-51-3)) (6.89 g, 41 mmol) and imidazole (8.69 g, 127 mmol) in N,N-dimethylformamide (20 mL) at 0° C. was added tert-butyl(chloro)dimethylsilane (10.73 g, 68 mmol) and the mixture was stirred and allowed to reach 23° C. overnight. The reaction mixture was poured into water, extracted twice with tert-butylmethyl ether, washed with saturated NaCl-solution, dried over sodium sulfate, filtered off and evaporated to give a brown liquid, which was purified by a silica gel column chromatography with heptane/ethyl acetate 1:4 to give an orange solid (9.72 g, 84%).

INTERMEDIATE 2 tert-Butyl-(2-isothiocyanato-6-nitro-benzyloxy)-dimethyl-silane

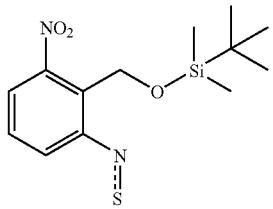

To a mixture of 2-(tert-butyl-dimethyl-silanyloxymethyl)-3-nitro-phenylamine (intermediate 1) (9.7 g, 34 mmol) and solid sodium hydrogen carbonate (14.4 g, 172 mmol) in methylene chloride (220 mL) at 0° C. was added thiophosgene (97%, 2.9 mL, 37 mmol), the cooling bath was removed and the mixture was stirred at 23° C. for 16 h. Poured into ice water (300 mL), separated phases, dried organic layer over sodium sulfate. Removal of the solvent in vacuum left a light brown oil (11 g, 99%).

INTERMEDIATE 3

3-Bromo-2-(tert-butyl-dimethyl-silanyloxymethyl)-phenylamine

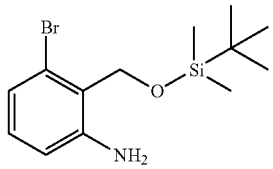

The title compound, light yellow oil, MS (ES) m/e=315.0 [(M)$^+$], was prepared from (2-amino-6-bromo-phenyl)-methanol [CAS No. 861106-92-5] and tert-butyl(chloro)dimethylsilane according to the procedure described for intermediate 1.

INTERMEDIATE 4

(2-Bromo-6-isothiocyanato-benzyloxy)-tert-butyl-dimethyl-silane

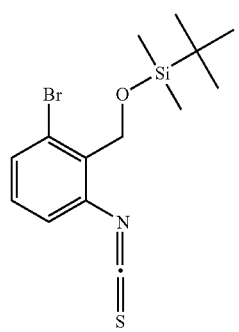

The title compound, yellow oil, MS (ES) m/e=357.0 [(M)$^+$], was prepared from 3-bromo-2-(tert-butyl-dimethyl-silanyloxymethyl)-phenylamine (intermediate 3) and thiophosgene according to the procedure described for intermediate 2.

EXAMPLE 1

(R)-Indan-1-yl-(5-nitro-4H-benzo[d][1,3]oxazin-2-yl)-amine

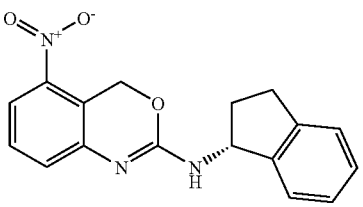

To a stirred solution of tert-butyl-(2-isothiocyanato-6-nitro-benzyloxy)-dimethyl-silane (intermediate 2) (3.0 g, 9.0 mmol) in acetonitrile (45 mL) at 23° C. was added R-(−)-1-aminoindane (1.24 g, 9.0 mmol) and the mixture was stirred at 23° C. for 45 min. Added tetrabutylammonium fluoride (1M in tetrahydrofurane, 9.25 mL, 9.0 mmol) and stirred at 23° C. for 1 h. Added 1-(3-dimethylaminopropyl)-3-ethylcarbodiimide hydrochloride (EDC.HCl) (2.71 g, 14 mmol) and refluxed for 4.5 h. Cooled to room temperature, diluted with ethyl acetate and water, added little 1 M NaH$_2$PO$_4$.2H$_2$O solution to achieve pH 4, separated phases, washed organic layer with brine and dried over sodium sulfate. Removal of the solvent in vacuum left a yellow foam, which was recrystallized from dichloromethane and diisopropylether to give the title compound as a yellow solid (1.94 g, 68%), MS (ISP) m/e=310.4 [(M+H)$^+$].

EXAMPLE 2

(R)—N²-Indan-1-yl-4H-benzo[d][1,3]oxazine-2,5-diamine

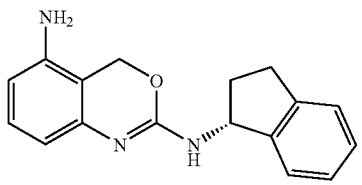

To a solution of (R)-indan-1-yl-(5-nitro-4H-benzo[d][1,3]oxazin-2-yl)-amine (example 1) (1.90 g, 6.1 mmol) in tetrahydrofuran (250 mL) at 23° C. were added three Pasteur pipettes of Raney-Nickel (ready to use 10% suspension in water) and the mixture was vigourously stirred under an atmospheric pressure of hydrogen for 23 h. The catalyst was filtered off, washed with tetrahydrofuran, the solvent was removed in vacuum to give the title compound as a light yellow foam (1.81 g, 99%), MS (ISP) m/e=280.4 [(M+H)⁺].

EXAMPLE 3

N²-(4-Methoxy-2,3-dihydro-benzofuran-3-yl)-4H-benzo[d][1,3]oxazine-2,5-diamine

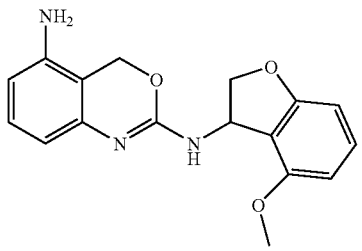

The title compound, MS (ISP) m/e=312.0 [(M+H)⁺], was prepared from tert-butyl-(2-isothiocyanato-6-nitro-benzyloxy)-dimethyl-silane (intermediate 2) and 4-methoxy-2,3-dihydro-benzofuran-3-ylamine according to the procedure described for example 1 and 2.

EXAMPLE 4

2-(4-Chloro-phenyl)-N-[2-((R)-indan-1-ylamino)-4H-benzo[d][1,3]oxazin-5-yl]-acetamide

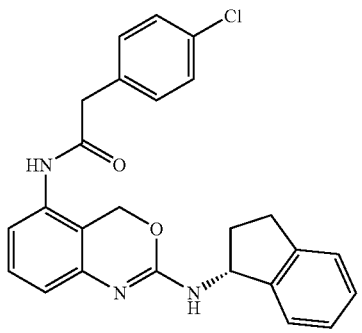

4-Chlorophenylacetic acid (122 mg, 0.65 mmol), N,N-diisopropyl ethyl amine (245 mg, 1.9 mmol) and 2-(1H-benzotriazole-1-yl)-1,1,3,3-tetramethyluronium tetrafluoroborate (254 mg, 0.79 mmol) were dissolved in dichloromethane (5 mL) and dimethylformamide (1 mL). The reaction mixture was stirred at room temperature for 30 minutes. (R)—N²-Indan-1-yl-4H-benzo[d][1,3]oxazine-2,5-diamine (example 2) (150 mg, 0.54 mmol) was added and stirring was continued overnight. The reaction mixture was diluted with water and extracted twice with dichloromethane. The combined organic phases were dried over sodium sulfate and evaporated. The crude product was recrystallized from isopropanol and diisopropylether. The title compound (95 mg, 41%) was obtained as a white solid; MS: m/e=430.5 (M–H⁺).

EXAMPLE 5

3,5-Difluoro-N-[2-((R)-indan-1-ylamino)-4H-benzo[d][1,3]oxazin-5-yl]-benzenesulfonamide

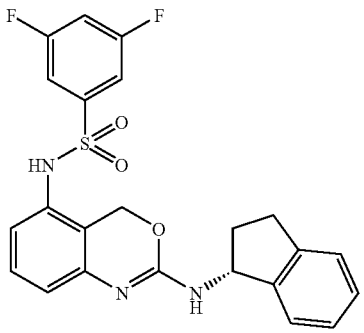

(R)—N²-Indan-1-yl-4H-benzo[d][1,3]oxazine-2,5-diamine (example 2) (150 mg, 0.54 mmol) was dissolved in 5 mL pyridine and 3,5-difluoro-benzenesulfonyl chloride (112 mg, 0.53 mmol) was added. The reaction mixture was stirred at room temperature overnight. 1N HCl was added until pH5. The mixture was extracted three times with ethyl acetate (50 mL each). The organic phases ware pooled, dried with sodium sulfate, filtered and evaporated. The crude product was purified by a silica gel column chromatography with heptane/ethyl acetate 1:1 to give a white solid (24 mg, 9%), MS: m/e=456.0 (M+H⁺).

EXAMPLE 6

3,5-Difluoro-N-[2-(4-methoxy-2,3-dihydro-benzofuran-3-ylamino)-4H-benzo[d][1,3]oxazin-5-yl]-benzenesulfonamide

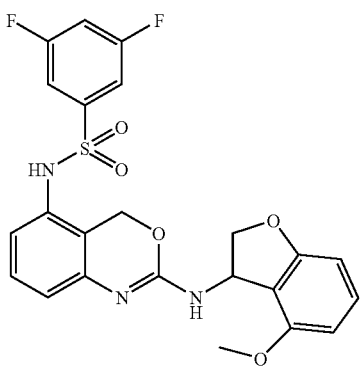

The title compound, MS (ISP) m/e=488.0 [(M+H)⁺], was prepared from N²-(4-methoxy-2,3-dihydro-benzofuran-3-yl)-4H-benzo[d][1,3]oxazine-2,5-diamine (example 3) and 3,5-difluoro-benzenesulfonyl chloride according to the procedure described for example 5.

EXAMPLE 7

Cyclopropanesulfonic acid [2-((R)-indan-1-ylamino)-4H-benzo[d][1,3]oxazin-5-yl]-amide

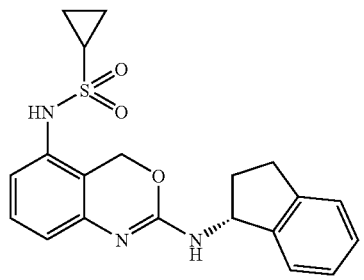

The title compound, MS (ISP) m/e=384.1 [(M+H)+], was prepared from (R)—N²-indan-1-yl-4H-benzo[d][1,3]oxazine-2,5-diamine (example 2) and cyclopropylsulfonyl chloride according to the procedure described for example 5.

EXAMPLE 8

N-[2-((R)-Indan-1-ylamino)-4H-benzo[d][1,3]oxazin-5-yl]-methanesulfonamide

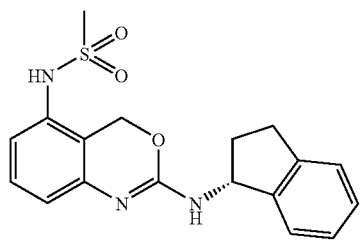

The title compound, MS (ISP) m/e=358.0 [(M+H)+], was prepared from (R)—N²-indan-1-yl-4H-benzo[d][1,3]oxazine-2,5-diamine (example 2) and methanesulfonyl chloride according to the procedure described for example 5.

EXAMPLE 9

(5-Chloro-4H-benzo[d][1,3]oxazin-2-yl)-(R)-indan-1-yl-amine

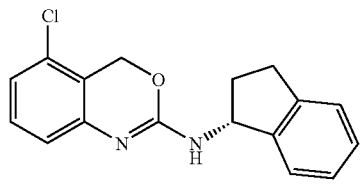

To a stirred solution of commercially available 2-amino-6-chlorobenzyl alcohol (CAS-no. 39885-08-0) (315 mg, 2 mmol) in tetrahydrofuran (4 ml) at 23° C. was added commercially available (R)-(−)-1-indanyl isothiocyanate (CAS-no. 737000-97-4) (324 ul, 2 mmol) and the mixture was stirred at 23° C. for 18 h, then at reflux for another 3 h. Cooled to 23° C., the solvent was removed in vacuum, the residue was dissolved in acetonitrile (4 ml), added dicyclohexylcarbodiimide (DCC) (619 mg, 3.0 mmol) and refluxed for 2 h. Cooled to room temperature, diluted with ethyl acetate and water, added little 1 M NaH₂PO₄.2H₂O solution to achieve pH 4, separated phases, washed organic layer with brine and dried over sodium sulfate. Removal of the solvent in vacuum left a yellow foam, which was purified by silica gel flash chromatography with n-heptane and ethyl acetate to give the title compound as a light yellow oil (215 mg, 36%), MS (ISP) m/e=299.1 [(M+H)+].

EXAMPLE 10

(5-Bromo-4H-benzo[d][1,3]oxazin-2-yl)-(R)-indan-1-yl-amine

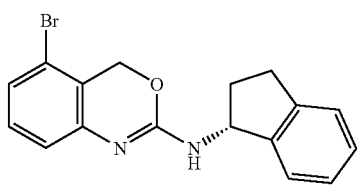

The title compound, light brown gum, MS (ISP) m/e=342.9 [(M+H)+], was prepared from (2-bromo-6-isothiocyanato-benzyloxy)-tert-butyl-dimethyl-silane (intermediate 4) and R-(−)-1-aminoindane according to the procedure of example 1.

EXAMPLE 11

2-((R)-Indan-1-ylamino)-4H-benzo[d][1,3]oxazine-5-carbonitrile

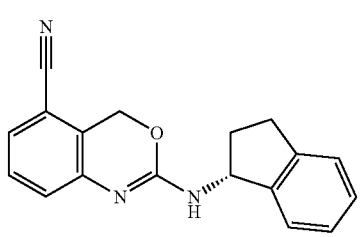

A stirred mixture of (5-bromo-4H-benzo[d][1,3]oxazin-2-yl)-(R)-indan-1-yl-amine (Example 10) (1.03 g, 3.79 mmol), zinc cyanide (528 mg, 4.5 mmol) and tetrakis-(triphenylphosphine)-palladium (347 mg, 0.3 mmol) in DMF (9 ml) was heated at 160° C. for 15 min in a microwave reactor. The reaction mixture was poured into water (50 ml) and extracted with ethyl acetate (2×50 ml). The combined organic layers were washed with brine (2×40 ml), dried (MgSO₄) and evaporated. The crude product was purified by flash chroma-

EXAMPLE 12

(5-Cyclopropyl-4H-benzo[d][1,3]oxazin-2-yl)-(R)-indan-1-yl-amine

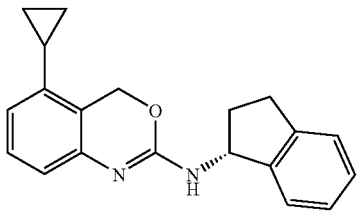

A stirred mixture of (5-bromo-4H-benzo[d][1,3]oxazin-2-yl) -(R)-indan-1-yl-amine (Example 10) (171.6 mg, 0.5 mmol), cyclopropylboronic acid (85.9 mg, 1.0 mmol), tricyclohexylphosphine (28 mg, 0.1 mmol), potassiumphosphate (371.5 mg, 1.75 mmol) and palladium actetate (11.2 mg, 0.05 mmol) in toluene (2 ml) and water (0.1 ml) was heated in a sealed tube at 110° C. for 17 h. The reaction mixture was poured into water (20 ml), extracted with ethyl acetate (2×30 ml). The combined organic layers were washed with water (20 ml) and brine (20 ml), dried (MgSO$_4$) and evaporated. Further purification by flash chromatography (ethyl acetate/heptane) on silica gel and crystallization (dichloromethane/heptane) yielded the title compound as colorless gum (83 mg, 49%). MS (ISP): m/e=305.2 (M+H$^+$).

EXAMPLE 13

[5-(4-Fluoro-phenyl)-4H-benzo[d][1,3]oxazin-2-yl]-(R)-indan-1-yl-amine

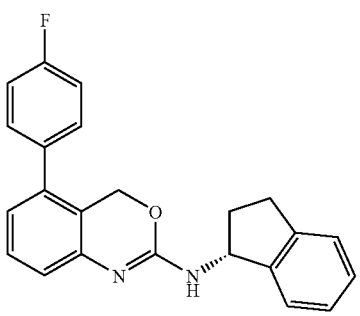

A stirred mixture of (5-bromo-4H-benzo[d][1,3]oxazin-2-yl) -(R)-indan-1-yl-amine (Example 10) (171.6 mg, 0.5 mmol), 4-fluorophenyl-boronic acid (84 mg, 0.6 mmol), 1M sodium carbonate solution (1.25 ml, 1.25 mmol), tetarkis (triphenylphosphine)palladium (17.3 mg, 0.015 mmol) in 1,2-dimethoxy-ethane (2.5 ml) was heated at 80° C. for 17 h. The reaction mixture was poured into water (20 ml), extracted with ethyl acetate (2×30 ml). The combined organic layers were washed with water (20 ml) and brine (20 ml), dried (MgSO$_4$) and evaporated. Further purification by flash chromatography (ethyl acetate/heptane) on silica gel yielded the title compound as white foam (164 mg, 92%). MS (ISP) m/e=359.1 [(M+H)$^+$].

EXAMPLE 14

N$^5$-(4-Fluoro-phenyl)-N$^2$—(R)-indan-1-yl-4H-benzo[d][1,3]oxazine-2,5-diamine

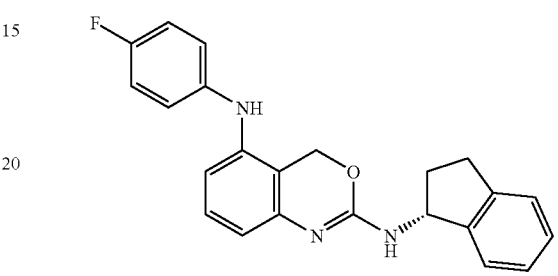

A mixture of (5-bromo-4H-benzo[d][1,3]oxazin-2-yl)-(R)-indan -1-yl-amine (Example 10) (343 mg, 1.0 mmol), commercially available 4-fluoro-aniline (222 mg, 2.0 mmol), XPhos (95 mg, 0.2 mmol), palladium-acetate (22 mg, 0.1 mmol), sodium tert.-butylate (192 mg, 2.0 mmol), tert-butanol (1 ml) and toluene (5 ml) was heated in a sealed tube at 120° C. for 16 h. The reaction mixture was poured into water (50 ml) and extracted with ethyl acetate (2×40 ml). The combined organic layers were washed with water (20 ml) and brine (20 ml), dried (MgSO$_4$) and evaporated. Further purification of the crude product by flash chromatography on silica gel (ethyl acetate/heptane) yielded the title compound (40 mg, 11%) as yellow foam. MS (ISP) m/e=374.2 [(M+H)$^+$].

EXAMPLE 15

N$^5$-(4-Chloro-phenyl)-N$^2$—(R)-indan-1-yl-4H-benzo[d][1,3]oxazine-2,5-diamine

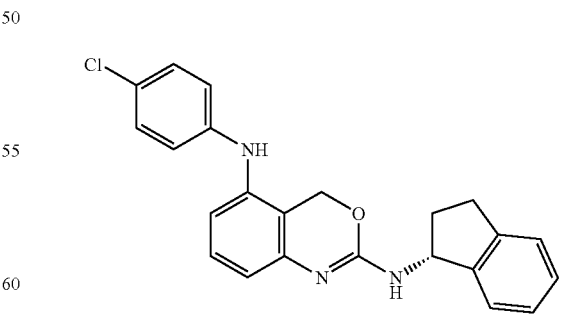

The title compound, yellow foam, MS (ISP) m/e=390.2 [(M+H)$^+$], was prepared from (5-bromo-4H-benzo[d][1,3]oxazin-2-yl)-(R)-indan-1-yl-amine (Example 10) and 4-chloroaniline according to the procedure of example 14.

The invention claimed is:
1. A compound of formula (I)

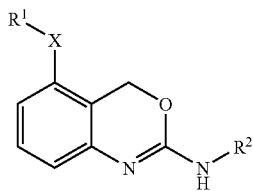

(I)

wherein:
X is a bond, —NH—, —NH—S(O)$_2$—, or —NH—C(O)—CH$_2$—;
R$^1$ is halo, C$_{1-7}$-alkyl, —NR$^a$R$^b$, cyano, nitro, or is phenyl or 3- to 8-membered cycloalkyl, each of which is optionally substituted by one or more halo;
R$^2$ is cycloalkyl or a 5- or 6-membered heterocycloalkyl, each optionally with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;
R$^a$ and R$^b$ is each independently hydrogen or C$_{1-7}$-alkyl;
or a pharmaceutically acceptable salt thereof.

2. The compound according to claim 1, wherein
X is a bond, —NH—, —NH—S(O)$_2$—, or —NH—C(O)—CH$_2$—;
R$^1$ is halo, C$_{1-7}$-alkyl, —NH$_2$, cyano, nitro, cyclopropyl, or phenyl optionally substituted by one or more halo;
R$^2$ is cyclopentyl or a 5- or 6-membered heterocycloalkyl, each optionally anellated with phenyl, which is optionally substituted with one or more C$_{1-7}$-alkoxy.

3. The compound according to claim 2, wherein
X is a bond, —NH—, or —NH—S(O)$_2$—;
R$^1$ is C$_{1-3}$-alkyl, —NH$_2$, cyclopropyl, or phenyl optionally substituted by one or more halo; R$^2$ is

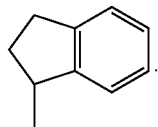

4. The compound according to claim 1, wherein X is —NH— or —NH—C(O)—CH$_2$—.

5. The compound according to claim 1, wherein R$^1$ is halo, C$_{1-7}$-alkyl, —NH$_2$, cyano, nitro, 3- to 8-membered cycloalkyl or phenyl substituted by one or more halo.

6. The compound according to claim 5, wherein R$^1$ is C$_{1-7}$-alkyl, —NH$_2$, 3- to 8-membered cycloalkyl, or phenyl substituted by one or two halo.

7. The compound according to claim 6, wherein R$^1$ is methyl, NH$_2$, 4-fluoro-phenyl, 4-chloro-phenyl, 3,5-difluoro-phenyl or cyclopropyl.

8. The compound according to claim 1, wherein R$^2$ is 3-8 membered cycloalkyl or 5- or 6-membered heterocycloalkyl anellated with phenyl, which is optionally substituted with one or more C$_{1-7}$-alkoxy.

9. The compound according to claim 8, wherein R$^2$ is 3-8 membered cycloalkyl anellated with phenyl.

10. The compound according to claim 9, wherein R$^2$ is indan-1-yl.

11. The compound according to claim 1, wherein R$^2$ is

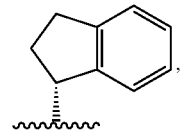

and wherein R$^2$ is present as (R)-stereoisomer.

12. The compound according to claim 1, wherein
X is a bond, —NH—, —NH—S(O)$_2$—, or —NH—C(O)—CH$_2$—;
R$^1$ is halo, C$_{1-7}$-alkyl, —NR$^a$R$^b$, cyano, nitro, or is phenyl or 3- to 8-membered cycloalkyl, each of which is optionally substituted by one or more halo;
R$^2$ is cyclopentyl or a 5- or 6-membered heterocycloalkyl, each optionally with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;
R$^a$ and R$^b$ is each independently hydrogen or C$_{1-7}$-alkyl;
or a pharmaceutically acceptable salt thereof.

13. The compound according to claim 1, selected from the group consisting of:
5-Chloro-4H-benzo[d][1,3]oxazin-2-yl)-(R)-indan-1-yl-amine;
(R)-Indan-1-yl-(5-nitro-4H-benzo[d][1,3]oxazin-2-yl)-amine;
(R)—N$^2$-Indan-1-yl-4H-benzo[d][1,3]oxazine-2,5-diamine;
N$^2$-(4-Methoxy-2,3-dihydro-benzofuran-3-yl)-4H-benzo[d][1,3]oxazine-2,5-diamine;
2-(4-Chloro-phenyl)-N-[2-((R)-indan-1-ylamino)-4H-benzo[d][1,3]oxazin-5-yl]-acetamide;
3,5-Difluoro-N-[2-((R)-indan-1-ylamino)-4H-benzo[d][1,3]oxazin-5-yl]-benzenesulfonamide;
3,5-Difluoro-N-[2-(4-methoxy-2,3-dihydro-benzofuran-3-ylamino)-4H-benzo[d][1,3]oxazin-5-yl]-benzenesulfonamide;
Cyclopropanesulfonic acid [2-((R)-indan-1-ylamino)-4H-benzo[d][1,3]oxazin-5-yl]-amide;
(5-Bromo-4H-benzo[d][1,3]oxazin-2-yl)-(R)-indan-1-yl-amine;
N-[2-((R)-Indan-1-ylamino)-4H-benzo[d][1,3]oxazin-5-yl]-methanesulfonamide;
2-((R)-Indan-1-ylamino)-4H-benzo[d][1,3]oxazine-5-carbonitrile;
(5-Cyclopropyl-4H-benzo[d][1,3]oxazin-2-yl)-(R)-indan-1-yl-amine;

[5-(4-Fluoro-phenyl)-4H-benzo[d][1,3]oxazin-2-yl]-(R)-indan-1-yl-amine;

$N^5$-(4-Fluoro-phenyl)-$N^2$—(R)-indan-1-yl-4H-benzo[d][1,3]oxazine-2,5-diamine; and $N^5$-(4-Chloro-phenyl)-$N^2$—(R)-indan-1-yl-4H-benzo[d][1,3]oxazine-2,5-diamine, or a pharmaceutically acceptable salt thereof.

14. The compound according to claim 13, selected from the group consisting of:

(R)—$N^2$-Indan-1-yl-4H-benzo[d][1,3]oxazine-2,5-diamine;

3,5-Difluoro-N-[2-((R)-indan-1-ylamino)-4H-benzo[d][1,3]oxazin-5-yl]-benzenesulfonamide;

Cyclopropanesulfonic acid [2-((R)-indan-1-ylamino)-4H-benzo[d][1,3]oxazin-5-yl]-amide;

N-[2-((R)-Indan-1-ylamino)-4H-benzo[d][1,3]oxazin-5-yl]-methanesulfonamide;

$N^5$-(4-Fluoro-phenyl)-$N^2$—(R)-indan-1-yl-4H-benzo[d][1,3]oxazine-2,5-diamine; and $N^5$-(4-Chloro-phenyl)-$N^2$—(R)-indan-1-yl-4H-benzo[d][1,3]oxazine-2,5-diamine, or a pharmaceutically acceptable salt thereof.

15. A pharmaceutical composition comprising a therapeutically effective amount of a compound of formula I

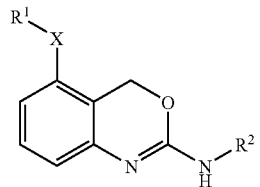

(I)

wherein:

X is a bond, —NH—, —NH—S(O)$_2$—, or —NH—C(O)—CH$_2$—;

$R^1$ is halo, C$_{1-7}$-alkyl, —NR$^a$R$^b$, cyano, nitro, or is phenyl or 3- to 8-membered cycloalkyl, each of which is optionally substituted by one or more halo;

$R^2$ is cycloalkyl or a 5- or 6-membered heterocycloalkyl, each optionally with phenyl or a 5- or 6-membered heteroaryl, wherein the phenyl or 5- or 6-membered heteroaryl each is optionally and independently substituted with one or more halo, C$_{1-7}$-alkyl and/or C$_{1-7}$-alkoxy;

$R^a$ and $R^b$ is each independently hydrogen or C$_{1-7}$-alkyl;

or a pharmaceutically acceptable salt thereof and a pharmaceutically acceptable carrier.

* * * * *